(12) United States Patent
Hart et al.

(10) Patent No.: US 8,951,277 B2
(45) Date of Patent: Feb. 10, 2015

(54) TAMPONADE TROCAR DEVICE AND METHOD

(71) Applicant: Applied Medical Resources Corporation, Rancho Santa Margarita, CA (US)

(72) Inventors: Charles C. Hart, Rancho Santa Margarita, CA (US); John R. Brustad, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 14/465,020

(22) Filed: Aug. 21, 2014

(65) Prior Publication Data

US 2014/0364832 A1   Dec. 11, 2014

Related U.S. Application Data

(63) Continuation of application No. 13/411,301, filed on Mar. 2, 2012, now Pat. No. 8,834,505, which is a continuation of application No. 12/106,920, filed on Apr. 21, 2008, now Pat. No. 8,142,467.

(51) Int. Cl.
  *A61B 17/34* (2006.01)
  *A61M 25/06* (2006.01)
  *A61M 25/10* (2013.01)
  *A61M 25/01* (2006.01)

(52) U.S. Cl.
  CPC ....... *A61M 25/0662* (2013.01); *A61M 25/1002* (2013.01); *A61M 25/10185* (2013.11); *A61B 17/3421* (2013.01); *A61M 25/0102* (2013.01); *A61M 2025/1068* (2013.01); *A61M 2025/0681* (2013.01)
  USPC ........................................................ 606/185

(58) Field of Classification Search
  USPC ......... 604/93.01, 96.01, 103.03, 104, 164.01, 604/164.04, 264; 606/184, 185, 190–192, 606/198
  See application file for complete search history.

(56) References Cited

U.S. PATENT DOCUMENTS

| | | | |
|---|---|---|---|
| 1,621,159 A | 3/1927 | Evans |
| 3,344,791 A | 10/1967 | Foderick |
| 3,717,151 A | 2/1973 | Collett |
| 3,789,852 A | 2/1974 | Kim et al. |
| 3,970,090 A | 7/1976 | Loiacono |
| 4,315,512 A | 2/1982 | Fogarty |

(Continued)

FOREIGN PATENT DOCUMENTS

FR                748666            7/1933

*Primary Examiner* — Ashley Fishback
(74) *Attorney, Agent, or Firm* — Rimas T. Lukas

(57) ABSTRACT

A tamponade trocar includes an elongate balloon having a closed distal end and is adapted to expand from a small diameter to a large diameter. A cannula is positioned at a proximal portion within the balloon lumen. A rigid stylet is removably positioned within the balloon and cannula lumens. A distal end of the stylet supported balloon is inserted into a perforation in a body wall and advanced into a body cavity while the balloon is unexpanded. The balloon is expanded and the cannula is advanced to a distal portion of the balloon lumen and across the body wall. At this stage, the perforation is dilated and in compressive tamponade. The proximal portion of the balloon may be removed and a seal housing may be coupled to the proximal end of the cannula. The distal end of the balloon may be punctured and opened, making the trocar ready for use.

20 Claims, 14 Drawing Sheets

(56) References Cited

U.S. PATENT DOCUMENTS

| | | | |
|---|---|---|---|
| 4,411,655 | A | 10/1983 | Schreck |
| 4,699,611 | A | 10/1987 | Bowden |
| 4,762,130 | A | 8/1988 | Fogarty et al. |
| 4,861,334 | A | 8/1989 | Nawaz |
| 4,921,479 | A | 5/1990 | Grayzel |
| 5,122,122 | A | 6/1992 | Allgood |
| 5,139,511 | A | 8/1992 | Gill et al. |
| 5,147,316 | A | 9/1992 | Castillenti |
| 5,176,697 | A | 1/1993 | Hasson et al. |
| 5,257,975 | A | 11/1993 | Foshee |
| 5,320,611 | A | 6/1994 | Bonutti et al. |
| 5,352,199 | A | 10/1994 | Tower |
| 5,443,484 | A | 8/1995 | Kirsch et al. |
| 5,445,615 | A | 8/1995 | Yoon |
| 5,458,583 | A | 10/1995 | McNeely et al. |
| 5,472,429 | A | 12/1995 | Yoon |
| 5,487,730 | A | 1/1996 | Marcadis et al. |
| 5,496,345 | A | 3/1996 | Kieturakis et al. |
| 5,545,135 | A | 8/1996 | Iacob et al. |
| 5,549,625 | A | 8/1996 | Bircoll |
| 5,632,761 | A | 5/1997 | Smith et al. |
| 5,653,690 | A | 8/1997 | Booth et al. |
| 5,697,913 | A | 12/1997 | Sierocuk et al. |
| 5,697,946 | A | 12/1997 | Hopper et al. |
| 5,762,604 | A | 6/1998 | Kieturakis |
| 5,814,058 | A | 9/1998 | Carlson |
| 5,827,319 | A | 10/1998 | Carlson et al. |
| 5,836,913 | A | 11/1998 | Orth et al. |
| 5,944,691 | A | 8/1999 | Querns et al. |
| 6,015,421 | A | 1/2000 | Echeverry et al. |
| 6,277,066 | B1 | 8/2001 | Irwin |
| 6,325,812 | B1 | 12/2001 | Dubrul et al. |
| 6,432,085 | B1 | 8/2002 | Stellon et al. |
| 6,524,283 | B1 | 2/2003 | Hopper et al. |
| 6,613,038 | B2 | 9/2003 | Bonutti et al. |
| 6,808,492 | B2 | 10/2004 | Snyder |
| 6,860,892 | B1 | 3/2005 | Tanaka et al. |
| 6,989,018 | B2 | 1/2006 | Fogarty et al. |
| 2003/0216770 | A1 | 11/2003 | Persidsky et al. |
| 2004/0068228 | A1 | 4/2004 | Cunningham |
| 2004/0230218 | A1 | 11/2004 | Criscuolo et al. |
| 2004/0243167 | A1 | 12/2004 | Tanaka et al. |
| 2004/0249243 | A1 | 12/2004 | Kleiner |
| 2005/0165432 | A1 | 7/2005 | Heinrich |
| 2006/0149136 | A1 | 7/2006 | Seto et al. |

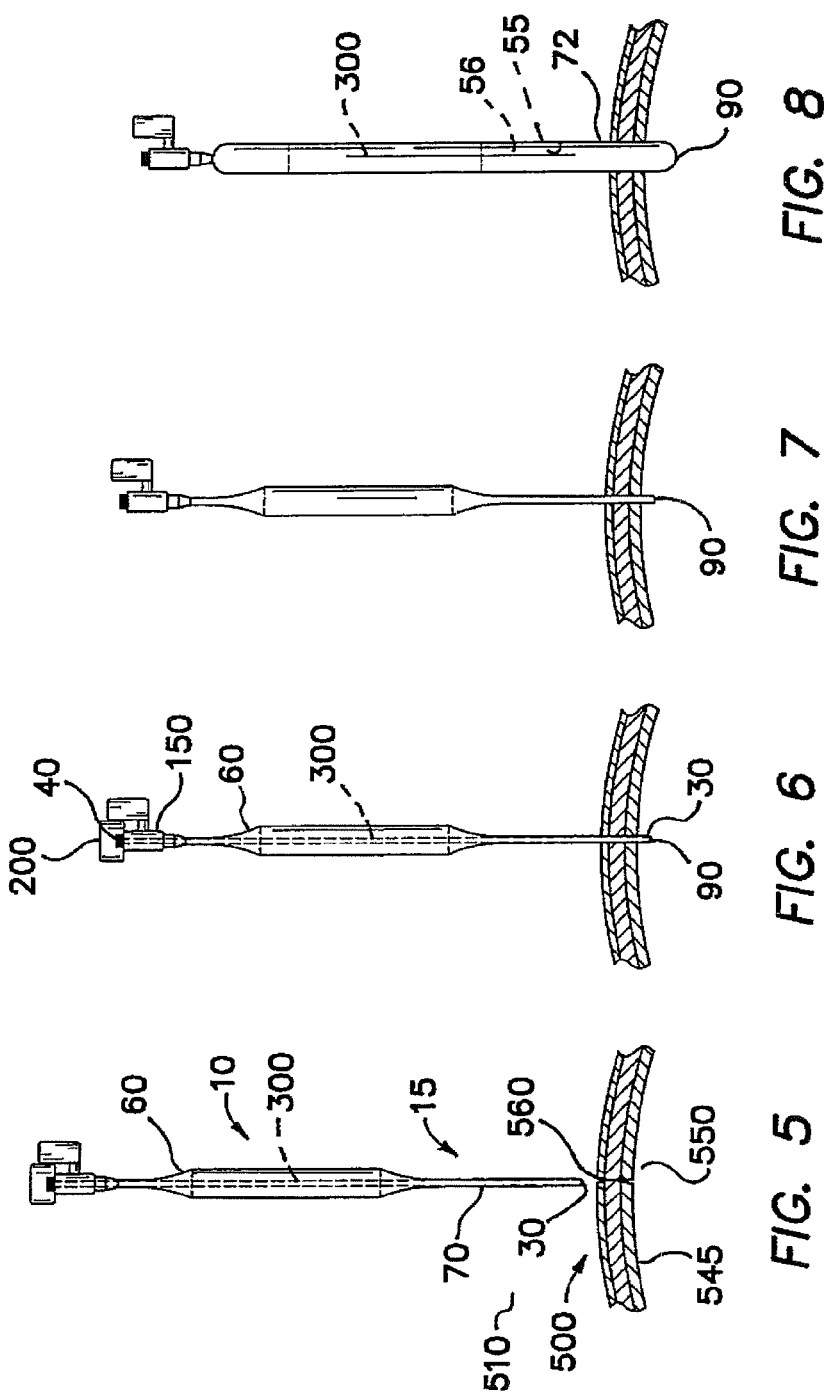

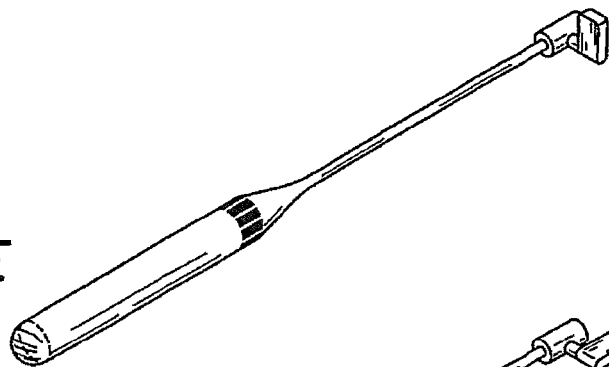
FIG. 15E
FIG. 15F
FIG. 15G
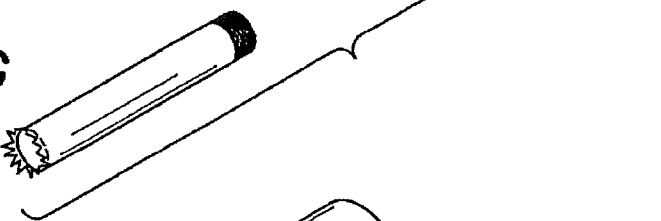
FIG. 15H
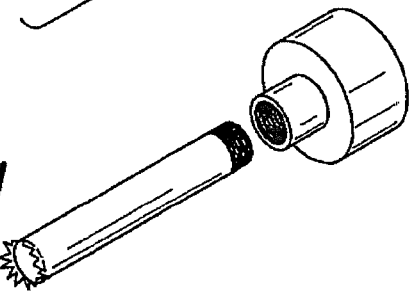
FIG. 15I
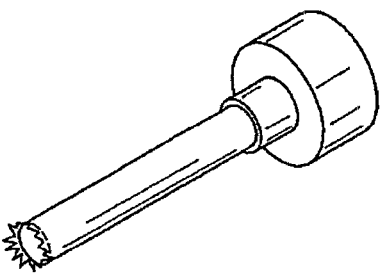

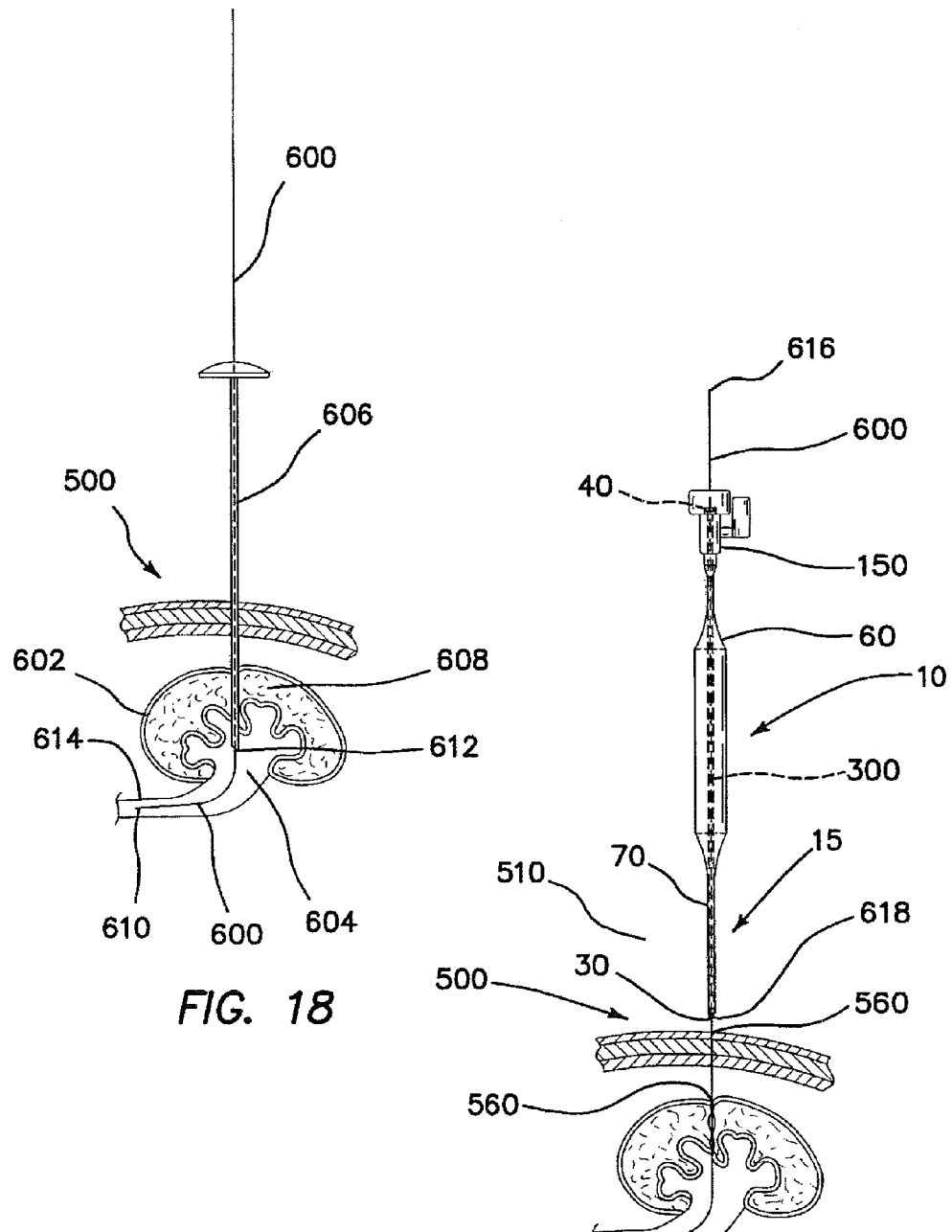

TAMPONADE TROCAR DEVICE AND METHOD

CROSS-REFERENCE TO RELATED APPLICATIONS

This application is a continuation of U.S. patent application Ser. No. 13/411,301 filed on Mar. 2, 2012 which is a continuation of U.S. patent application Ser. No. 12/106,920 filed on Apr. 21, 2008, now U.S. Pat. No. 8,142,467 all of which are incorporated herein by reference in their entireties.

BACKGROUND

As the use of laparoscopic surgery has grown, the tools available for use in laparoscopy continue to increase and have become quite sophisticated. Considerable effort and skill have been applied to the development of instruments and devices that make laparoscopy safe, effective and economical.

The trocars used to perform laparoscopic surgery receive much attention. The trocar is generally understood to be an assembly including a cannula, a seal housing and an obturator. The cannula is typically an elongate tubular structure that is sized and configured to traverse a biological body wall and communicate between external a biological body to a body cavity within the biological body. Cannulas that are presently used for laparoscopic procedures typically range in size from about 3 mm to about 15 mm in diameter and from about 6 cm to about 18 cm in length. The seal housing may include an enlarged proximal portion of the cannula or may be a separate component that is coupled to the proximal end of the cannula. The seal housing contains at least one substantially gastight seal that allows instruments to be passed through the cannula and utilized in the surgical procedure while maintaining internal pressure, or pneumoperitoneum, of the body cavity into which the cannula communicates. The obturator is typically an elongate sharpened device that is sized and configured to penetrate the body wall. The obturator is often inserted into the lumen of the cannula so that the cannula may be inserted into the body wall concurrently with the obturator. With the distal end of the cannula positioned within the body cavity, the obturator may be removed from the cannula and the trocar is ready for use as a surgical port through which appropriate instruments are used.

Although trocars have been, and continue to be, the subject of much invention, trocars are much the same as they have always been. Seals have improved, materials have evolved and manufacturing methods have resulted in more economical trocars, but there are still unmet needs. What has been needed is a trocar that does not require a relatively large force to penetrate the body wall, such as the abdominal wall, of a patient. Also needed is a trocar that substantially eliminates bleeding at the trocar site during the laparoscopic procedure.

One response to the need for reduced trocar penetration force has been advanced by the device disclosed in U.S. Pat. No. 5,431,676 to Dubrul, et al. (Dubrul, et al. '676). The device of Dubrul, et al. '676 includes a woven tubular sheath that is placed through a puncture or small incision in the body wall. With the sheath placed across the body wall, a trocar is advanced through the sheath and into the body cavity. Although the device of Dubrul, et al. '676 reduces the penetration force required to advance the trocar through the body wall, the penetration force is not reduced significantly and the force required to dilate the tissue adjacent the sheath can be overwhelming. Use of the device of Dubrul, et al. '676 requires the user to force a cannula and a blunt obturator through a collapsed, reinforced sheath that is confined circumferentially over its entire tissue-contacting length. In a muscular patient, this constrictive force can be significant. It is not uncommon for the force required to overcome the resistance to penetration to exceed eighteen (18) kilograms, even though in some cases a force of four and one-half (4.5) kilograms may be considered excessive.

SUMMARY

The present invention provides a device and method for significantly reducing the force required to place a trocar through a biological body wall. The present invention further provides a trocar device that significantly reduces or prevents bleeding at the trocar penetration site in the body wall.

In one aspect, a tamponade trocar includes an elongate balloon, a cannula, a rigid tensioning stylet, and a trocar seal housing. The balloon has a proximal end, a distal end, and a lumen that extends between the proximal and distal ends. The distal end of the balloon is closed and is gastight. The balloon is adapted to expand from a first, low-profile, small diameter condition to a second, fixed, large diameter condition. The cannula has a proximal end, a distal end, and a lumen that extends between the proximal and distal ends. The cannula is positioned within the lumen of the balloon at a first, proximal portion of the balloon. The stylet has a proximal end and a distal end and is removably positioned within the lumens of the balloon and the cannula. The distal end of the stylet is positioned at the distal end of the balloon and the proximal end of the stylet is positioned proximal to the proximal end of the balloon. The trocar seal housing is adapted to be coupled to the proximal end of the cannula. With the balloon in the first, low profile, small diameter condition, the cannula is prevented from transitioning positions within the lumen of the balloon. With the balloon in the second, fixed, large diameter condition, the internal diameter of the balloon is larger than the outside diameter of the cannula and the cannula is free to transition from the first, proximal portion of the balloon to a second, distal portion of the balloon.

In one facet, the application of inflation pressure at the proximal end of the balloon causes the expansion from the first, low-profile, small diameter condition to the second, fixed, large diameter condition. In another facet, the tamponade trocar includes a valve that is positioned proximate the proximal end of the balloon. The valve is adapted to communicate between the balloon lumen and the atmosphere external the balloon and the application of inflation pressure through the valve causes the expansion of the balloon from the first condition to the second condition. In this manner, the distal end of the stylet is positioned at the distal end of the balloon and the proximal end of the stylet is positioned proximal to the valve. In a further facet, the balloon is constructed of a non-distensible material, or alternatively, from at least one of polyethylene, polyurethane, and nylon. In an additional facet, the balloon has a length that is at least twice the length of the cannula, while in another facet the balloon has a length that is less than twice the length of the cannula. In one facet, the distal end of the balloon is rounded, while in another facet the distal end of the balloon is tapered. In an additional facet, the balloon has an elongated toroid shape that forms a tubular channel throughout the length of the balloon. The tubular channel of the balloon is coupled to an outer body portion of the balloon at a distal end of the outer body portion of the balloon and at a proximal portion of the outer body portion of the balloon.

Many of the attendant features of the present invention will be more readily appreciated as the same becomes better understood by reference to the following detailed description and considered in connection with the accompanying drawings in which like reference symbols designate like parts throughout.

BRIEF DESCRIPTION OF THE DRAWINGS

FIG. 5 is a side view depicting the device of the invention, including the cannula and stylet positioned within the unexpanded balloon or sheath and the cannula in the first, proximal portion of the balloon, ready for use to penetrate a biological body wall.

FIG. 6 is a side view depicting the distal portion of the balloon or sheath and stylet penetrating the biological body wall.

FIG. 7 is a side view depicting the device with the distal end of the unexpanded balloon positioned in the body cavity, the cannula positioned proximal the body wall and the stylet removed from the balloon or sheath.

FIG. 8 is a side view depicting the device with the balloon or sheath expanded and positioned within the body wall with the distal end of the balloon or sheath positioned in the body cavity and the cannula positioned proximal the body wall.

FIGS. 15A-15I depict a sequence of use for the trocar device of the present invention.

FIG. 18 is a side view depicting a needle inserted from outside a biological body into the renal pelvis of a kidney and a guide wire extending through the needle.

FIG. 19 is a side view depicting the device of FIGS. 16 and 17 advanced along the guide wire of FIG. 18, with the needle removed, including the cannula and stylet positioned within the unexpanded balloon or sheath and the cannula in the first, proximal portion of the balloon, ready for use to penetrate a biological body wall.

DETAILED DESCRIPTION

Figure 1:
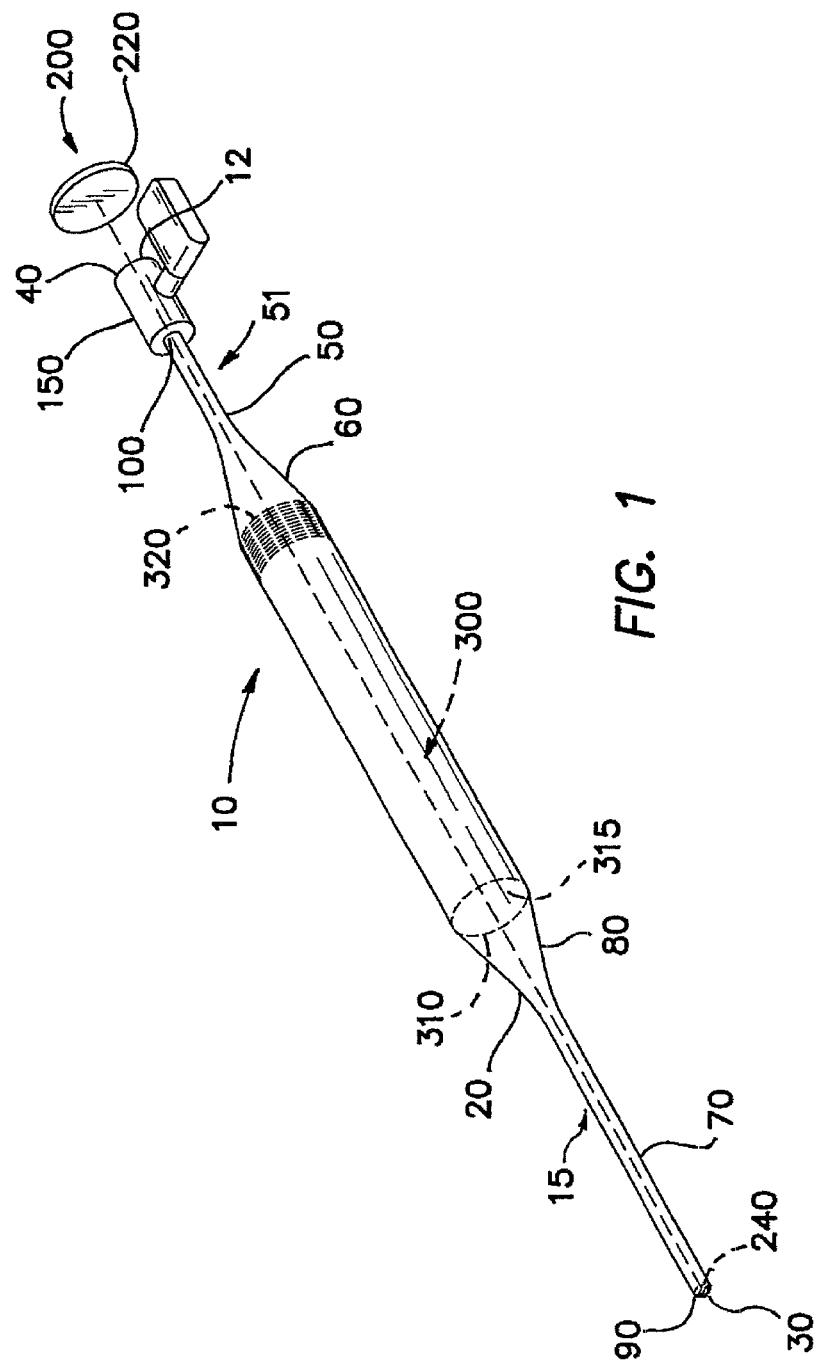
FIG. 1 is a perspective view depicting the device of the present invention including a cannula and a stylet positioned within an unexpanded balloon or sheath with the cannula positioned in a first, proximal portion of the balloon or sheath.

Turning now to the drawings, in which like reference numerals represent like or corresponding elements in the drawings, FIGS. 1-4 depict a tamponade trocar 10 having an elongate balloon or sheath 15, a cannula 300 and a tensioning stylet 200. The cannula 300 includes a first, proximal end 320, a second, distal end 310 and a lumen 315 extending between the proximal end and the distal end.

Figure 2:
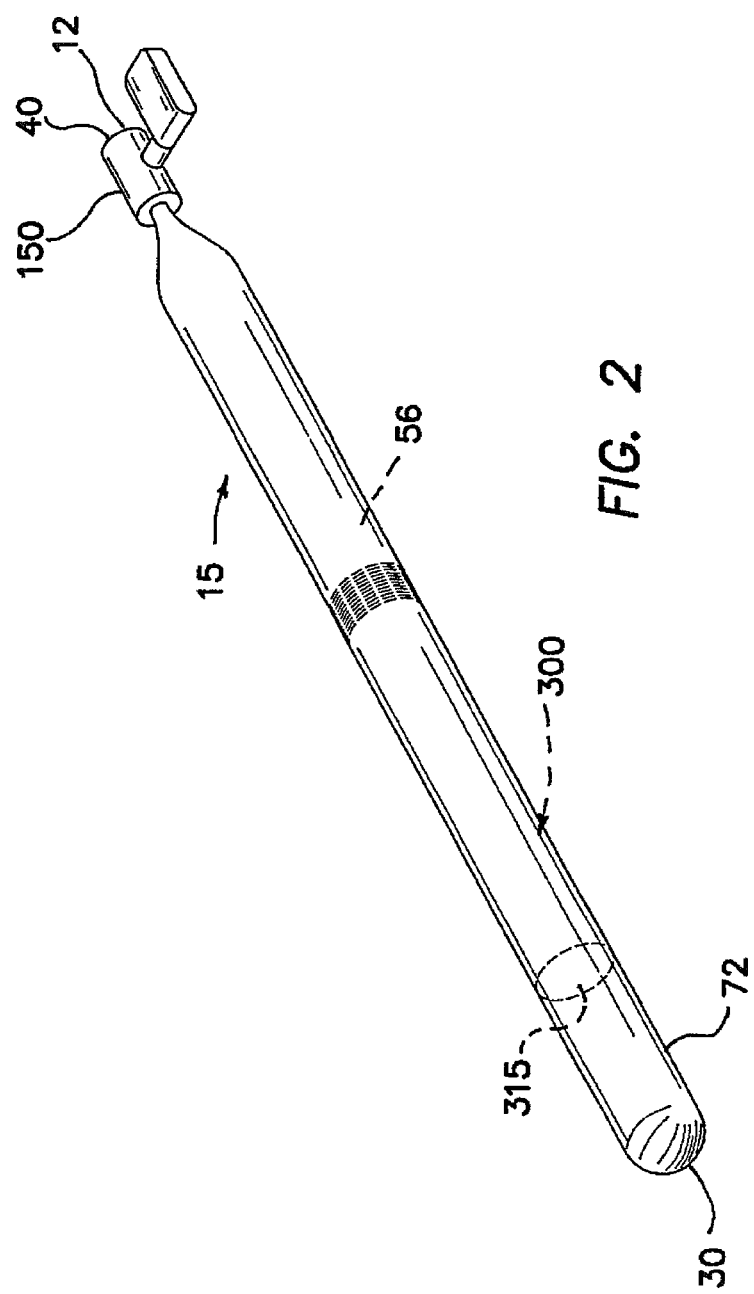
FIG. 2 is a perspective view depicting the cannula within an expanded balloon or sheath with the stylet removed and the cannula advanced toward a second, distal portion of the balloon or sheath.
Figure 3:
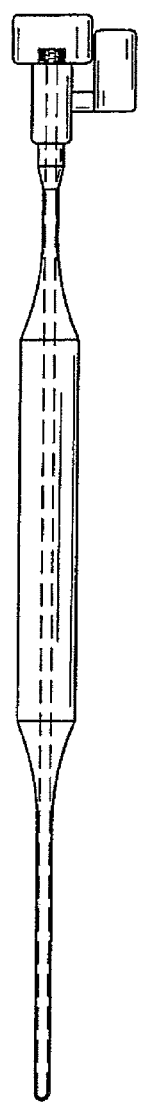
FIG. 3 is a side view depicting the cannula and stylet positioned in the unexpanded balloon or sheath with the cannula positioned in the first, proximal portion of the balloon or sheath.
Figure 4:
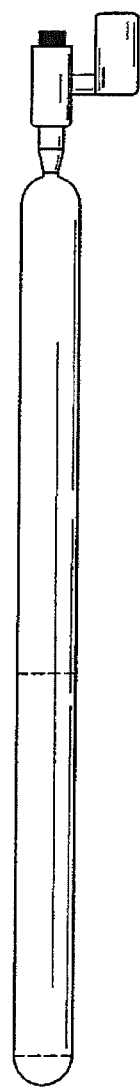
FIG. 4 is a side view depicting the cannula within the expanded balloon or sheath with the stylet removed and the cannula advanced to the second, distal portion of the balloon or sheath.
Figure 11:
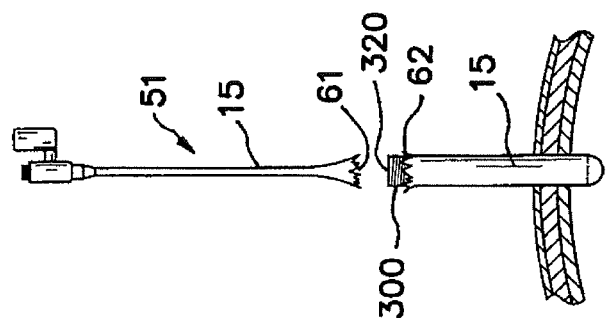
FIG. 11 is a side view depicting a proximal portion of the balloon or sheath separated and removed from the cannula.
Figure 10:
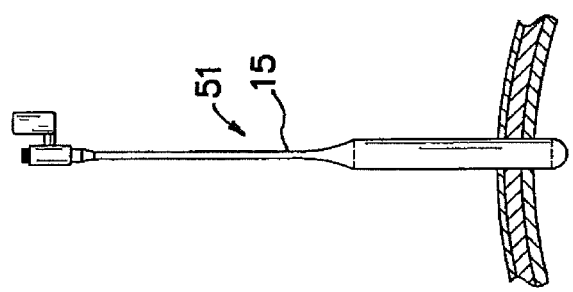
FIG. 10 is a side view depicting the balloon or sheath unexpanded with the balloon or sheath and the cannula positioned across the body wall and the distal ends of the balloon or sheath and the cannula positioned distal the inner surface of the body wall and in the body cavity.

The balloon or sheath 15 includes a first, proximal end 40, a second, distal end 30 and a lumen 56 extending between the proximal and distal ends. The distal end 30 of the balloon or sheath may be closed and substantially gastight. The distal end 30 of the balloon or sheath 15 may be rounded or tapered 90 to facilitate penetration through a previously existing breach 560 (FIGS. 6-14) through a body wall 500 and into a body cavity 550. The balloon or sheath 15 may be constructed of a substantially non-distensible material, such as polyethylene, polyurethane, or nylon and may be cross-linked to provide stability. The balloon or sheath 15 may be thick-walled and have a length that is at least about twice the length of the cannula 300. Those familiar with the art will recognize that the balloon 15 may be longer or shorter than about twice the length of the cannula 300 depending on the parameters for which the tamponade trocar 10 will be used and such lengths are contemplated as within the scope of the invention. A first, proximal portion 60 of the balloon or sheath 15 is sized and configured to contain the cannula 300. The balloon or sheath 15 is adapted to expand from a first, low-profile, small diameter condition 70 (FIGS. 1 and 3) to a second, substantially fixed, large diameter condition 72 (FIGS. 2 and 4). The internal diameter of the balloon or sheath 15 when the balloon is in the second, large diameter condition 72 is slightly larger than the outside diameter of the cannula 300 within it to facilitate transitioning of the cannula from the proximal portion 60 of the balloon or sheath to a second, distal portion 80 of the balloon or sheath. A valve 150 or seal may be positioned in the proximal portion 60 of the balloon or sheath 15, such as proximate the proximal end 40 of the balloon or sheath. The valve is adapted to communicate between the balloon lumen 56 and the atmosphere external the balloon. The transition from the first condition 70 to the second condition 72 may be accomplished by the application of inflation pressure at the proximal end 40 of the balloon or sheath 15 or the valve 150.

The pressure required to fully expand the high-pressure balloon or sheath 15 is substantially equivalent to the pressure required to expand a non-distensible balloon of the type used in angioplasty or other dilation driven therapies. The balloon or sheath 15 may be either undeveloped, having an unformed, thick-walled expandable tube, or it may be a preformed and folded tube. An unformed or undeveloped tube of the balloon or sheath 15 presents a smooth, small diameter profile but may require more inflation pressure than a preformed balloon or sheath 15. The preformed balloon or sheath 15 develops the ultimate expanded diameter at a lower pressure than for the unformed tube but may have a more irregular surface or a less than smooth profile. Either mode, however, permits a reduced portion 20, 50 for insertion through a perforation 560. When the balloon 15 is in the first, low profile, small diameter condition 70, the cannula 300 is substantially prevented from transitioning positions within the lumen 56 of the balloon. However, when the balloon 15 is expanded to the second, substantially fixed, large diameter condition 72, the cannula 300 is substantially free to transition to the second, distal portion 80 of the balloon.

The stylet 200 is substantially rigid and includes a proximal end 220 and a distal end 240. The stylet 200 is removably positioned within the lumen 56 of the balloon 15 and within the lumen 315 of the cannula 300. The distal end 240 of the stylet 200 is positioned at the distal end 30 of the balloon 15 and the proximal end 220 of the stylet is positioned proximal to the proximal end 40 of the balloon or sheath 15. Where the tamponade trocar device 10 includes the valve 150, the proximal end 220 of the stylet 200 may be positioned proximal to the valve. As will be discussed below, the stylet 200 may be hollow to facilitate insertion of a guide wire therethrough.

Figure 9:
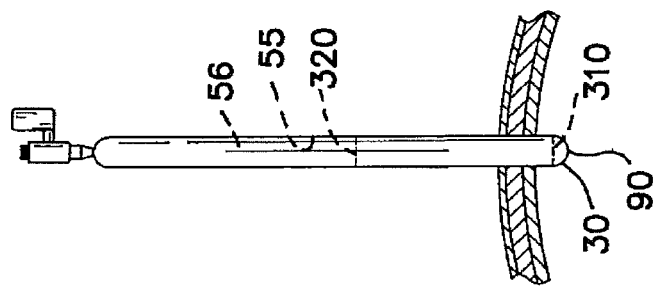
FIG. 9 is a side view depicting the device with the cannula advanced through the expanded balloon or sheath to a second, distal portion of the balloon or sheath and across the body wall with the distal end of the cannula positioned distal an inner surface of the body wall and the proximal end of the cannula positioned proximal the body wall.
Figure 14:
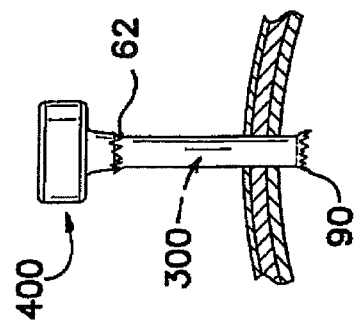
FIG. 14 is a side view depicting the trocar of the present invention placed across the body wall and into the body cavity and ready for use as a laparoscopic surgery port.
Figure 13:
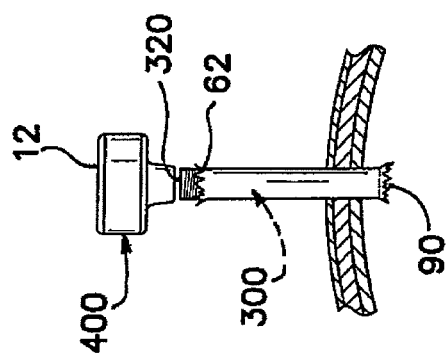
FIG. 13 is a side view depicting the distal end of the balloon after being pierced, the piercing device removed, a seal housing being coupled to the proximal end of the cannula, and the cannula in communication between the body cavity and external the body wall.
Figure 12:
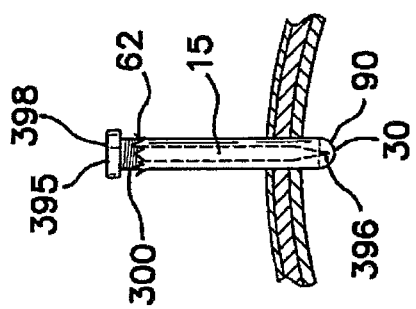
FIG. 12 is a side view depicting a piercing device inserted into the lumen of the cannula to pierce the distal end of the balloon or sheath.
Figure 15A:
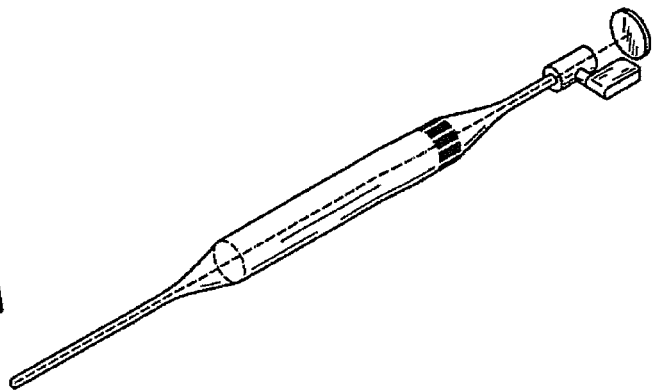
Figure 15B:
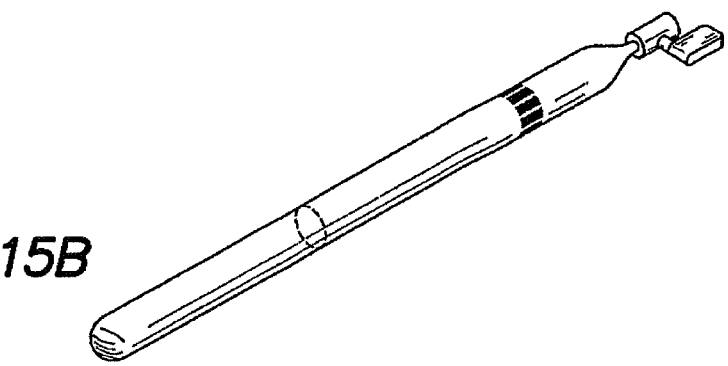
Figure 15C:
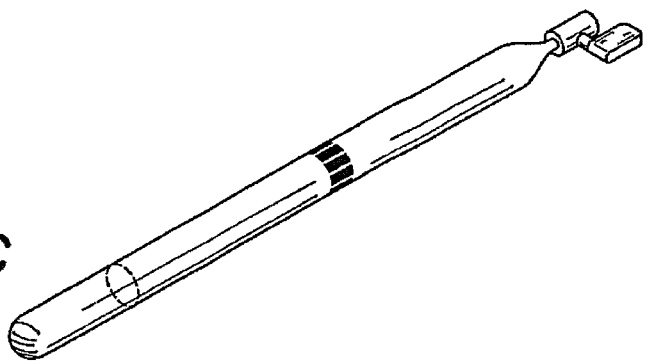
Figure 15D:
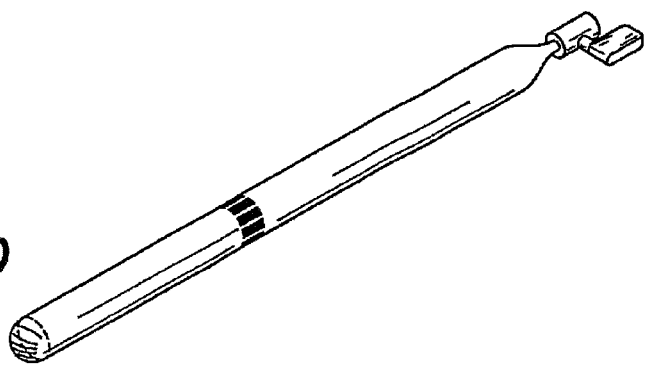

Referring to FIGS. 5 through 15, a method for placing the tamponade trocar device 10 within a biological body wall 500 is depicted. An insufflation needle (FIG. 18) creates a perforation 560 through the body wall 500 to the body cavity 550 and the body cavity is insufflated. The tamponade trocar device 10 is positioned external the body wall 500 with the distal end 30 of the balloon 15 proximate the perforation 560 through the body wall (FIG. 5). With the balloon 15 in the first, low-profile, small diameter condition 70 and the cannula 300 positioned in a first, proximal portion 60 in the balloon and proximal the body wall 500, the distal end 30 of the balloon of the tamponade trocar device is inserted into the perforation 560 in the body wall 500. The balloon 15 is advanced until the distal end 30 of the balloon of the device is distal an inner surface 545, or peritoneum, of the body wall 500 and within the body cavity 550 while the cannula 300 remains in the first, proximal portion 60 of the balloon and proximal the body wall (FIG. 6). No sharp obturator or stylet is required for the deployment of the tamponade trocar device. When the tamponade trocar device 10 is sufficiently advanced, the stylet 200 may be removed proximally from the proximal end 40 of the balloon 15 or from the valve 150 (FIG. 7). A pressurizing or filling source (not shown) is coupled to the proximal end 40 of the balloon 15 or to the valve 150 and the balloon is pressurized to the second, substantially fixed, large diameter condition 72 (FIG. 8). At this stage, the perforation 560 is fully dilated and in compressive tamponade. The inside diameter 55 of the balloon 15 allows for the free movement of the cannula 300 that has been provided in the lumen 56 of the balloon. With the balloon 15 expanded and the stylet 200 removed, the cannula 300 is free to transition positions within the lumen 56 of the balloon. For example, the cannula 300 may be advanced distally within the lumen 56 of the balloon so that the cannula is positioned across the body wall 500 with the proximal end 320 of the cannula positioned proximal the body wall and the distal end 310 of the cannula positioned distal the inner surface 545 of the body wall (FIG. 9). With the distal end 30 of the balloon 15 intact, there is no communication between the exterior 510 of the body and the interior of the body cavity 550 through the perforation 560 via the cannula 300. The balloon 15 is deflated (FIG. 10) or, as is the case with non-distensible balloons, depressurized to ambient pressure. The deflated, unexpanded, balloon 15 is severed (FIG. 11) at a position 61 proximate the proximal end 320 of the cannula 300 and the portion of the balloon proximal the point of severance 62 is removed from the remaining portion of the balloon. The portion 51 of the balloon 15 proximal the point of severance may be discarded. A piercing member 395 may be provided. The piercing member 395 includes a proximal end 398 and a distal, puncturing end 396. The piercing member 395 is adapted to fit through the cannula 300 and is of sufficient length to extend the length of the cannula and penetrate the distal end of the balloon 15. The distal end 396 of the piercing member 395 may be inserted into the proximal end 12 of the tamponade trocar device 10 and advanced distally through the tamponade trocar device until the distal, puncturing end of the piercing member punctures and opens the distal end 30 of the balloon 15. The sequence of steps may be adjusted so that the piercing member 395 is placed in the cannula after the final placement of a seal housing 400 in a coupling relationship with the proximal end 320 of the cannula 300 so that there is little or no loss of insufflation pressure or pneumoperitoneum during the process for inserting the tamponade trocar device 10 into the body wall 500. A trocar seal housing 400 (FIGS. 13 and 14) is coupled to the proximal end 320 of the cannula 300 and the trocar is ready for use as a surgical port.

Figures 16, 17:
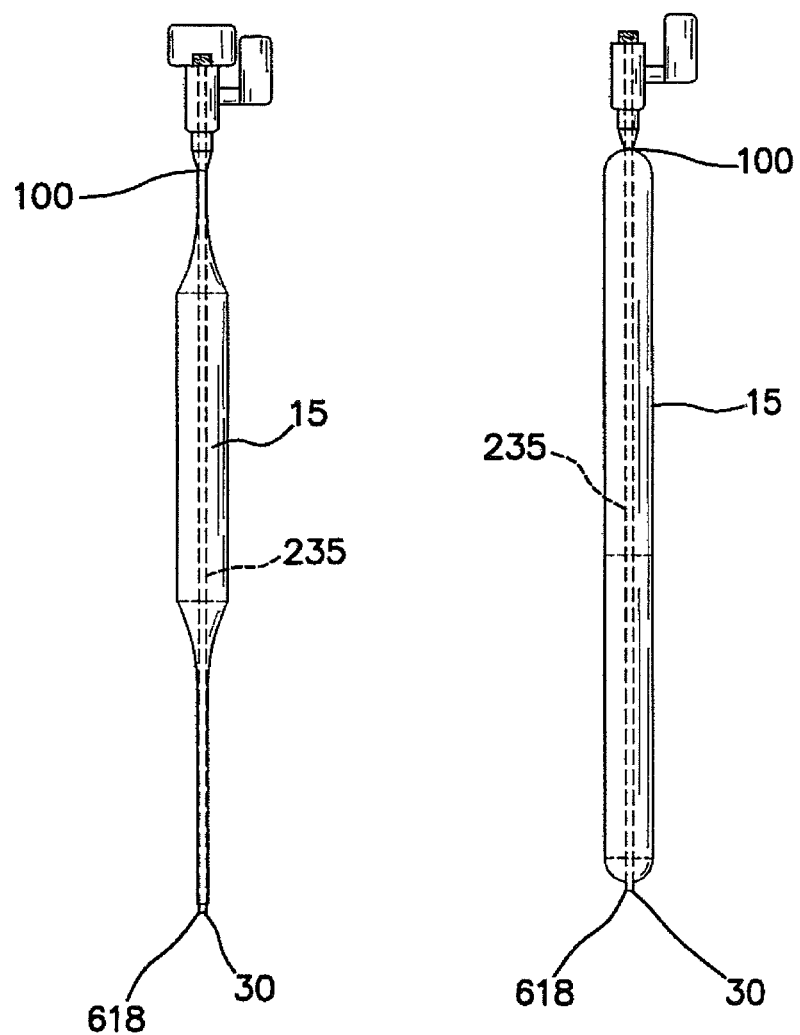
FIG. 16 is a side view depicting the trocar device of the present invention having a through lumen in the balloon or sheath with the balloon or sheath in the unexpanded condition.
FIG. 17 is a side view depicting the trocar device of FIG. 16 with the balloon or sheath in the expanded condition.

Referring to FIGS. 16 and 17, the balloon 15 may include a substantially toroid shape that forms a substantially tubular channel 235 throughout its length to facilitate advancing the distal end 30 of the balloon into the perforation 560 in the body wall 500 without first removing the needle from the body wall. As will be discussed in more detail below, the use of the tubular channel 235 also facilitates insertion of the tamponade trocar device 10 over a guide wire 600 that can be inserted, for example, into a cavity of a biological organ, such as the renal pelvis 604 of a kidney 602, to perform a surgical procedure, such as a percutaneous nephrolithotomy. The main, outer body portion of the balloon 15 is coupled to the tubular channel 235 at the distal end 30 of the outer body portion of the balloon and at a proximal portion 100 of the outer body portion of the balloon so that the expandable portion of the balloon surrounds the tubular channel through which insufflation occurs.

Percutaneous nephrolithotomy includes the use of a cannula placed into a kidney, such as in the renal pelvis, to remove kidney stones. Referring to FIGS. 18 through 28, a method for placing the tamponade trocar device 10 having the tubular channel 235 (FIGS. 16 and 17) within a biological body wall 500 and into the renal pelvis 604 of a kidney 602 is depicted. A needle 606 creates a perforation 560 through the body wall 500 and through the wall 608 of the kidney 602, thereby providing access to the renal pelvis 604. A guide wire 600 is inserted into a proximal end of the needle 606 and advanced therethrough until the distal end 610 of the guide wire is positioned distal to the distal end 612 of the needle (FIG. 18). The distal end 610 of the guide wire 600 may be advanced further than the renal pelvis 604, such as into the ureter 614. While maintaining the position of the guide wire 600 within the biological body, the needle 606 may be removed distally over the guide wire.

While maintaining the position of the guide wire 600 within the biological body, the proximal end 616 of the guide wire is inserted into the distal end 618 of the tubular channel 235 of the tamponade trocar device 10. While the tamponade trocar device 10 is positioned external the body wall 500, the tamponade trocar device is advanced distally over the guide wire 600 until the distal end 30 of the balloon 15 is positioned proximate the perforation 560 through the body wall and the proximal end 616 of the guide wire is positioned proximal to the proximal end 40 of the balloon 15 or valve 150 (FIG. 19).

Figures 20, 21:
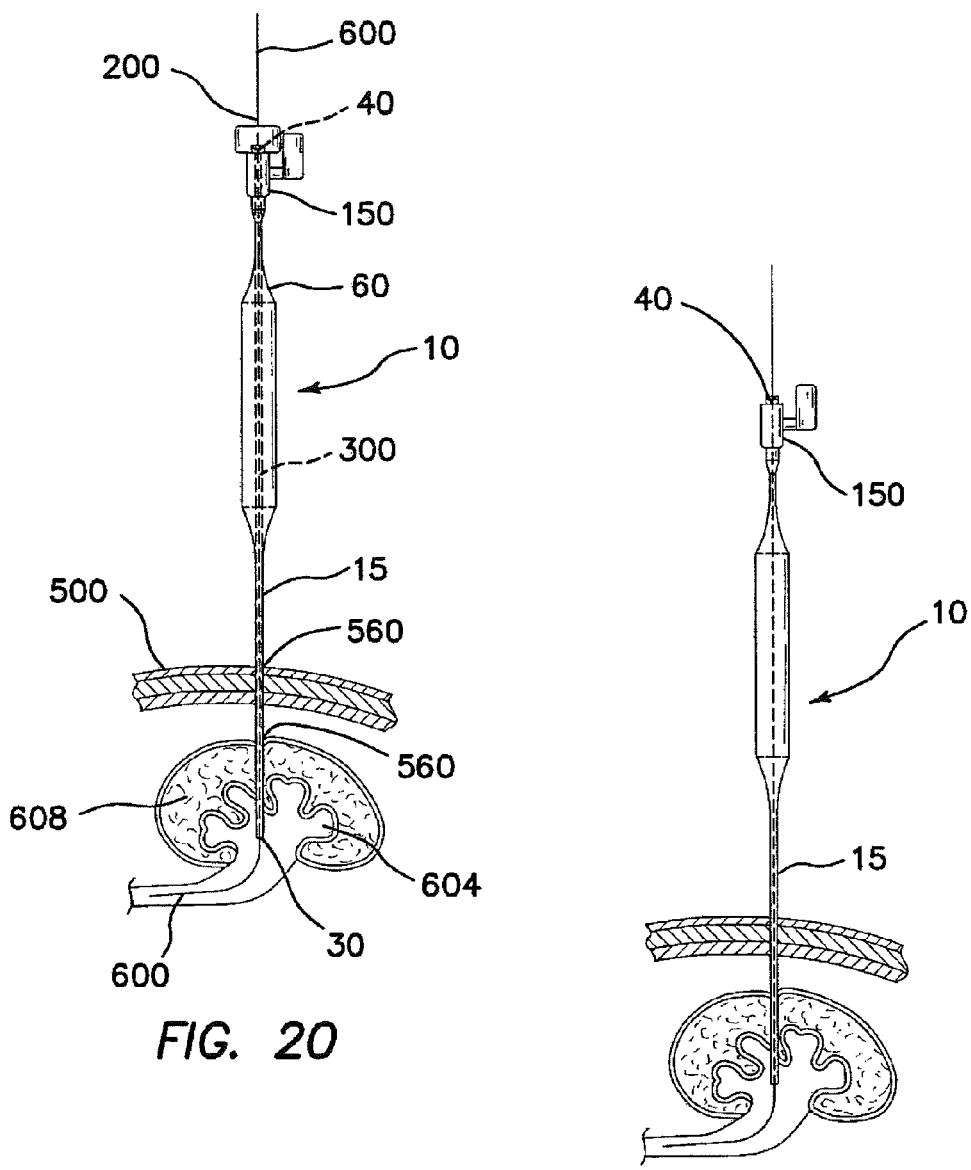
FIG. 20 is a side view depicting the trocar device of FIGS. 16 and 17 advancing along the guide wire of FIG. 18 and the distal portion of the balloon or sheath and stylet penetrating the biological body wall and kidney.
FIG. 21 is a side view depicting the device of FIGS. 16 and 17 with the distal end of the unexpanded balloon positioned in the renal pelvis of the kidney, the cannula positioned proximal the body wall, the guide wire in place and the stylet removed from the balloon or sheath.

With the balloon 15 in the first, low-profile, small diameter condition 70, the cannula 300 positioned in the first, proximal portion 60 of the balloon and proximal the body wall 500, and the guide wire 600 positioned through the tubular channel 235, the distal end 30 of the balloon of the tamponade trocar device 10 is advanced distally over the guide wire and inserted into the perforation 560 in the body wall 500 and the kidney wall 608. The balloon 15 is advanced until the distal end 30 of the balloon of the tamponade trocar device 10 is within the renal pelvis 604 while the cannula 300 remains in the first, proximal portion 60 of the balloon and proximal the body wall 500 (FIG. 20). The stylet 200 may be used during advancement of the balloon 15 to provide columnar strength to the balloon during insertion into the body. The stylet 200 may be hollow, thereby providing for insertion of the guide wire 600 therethrough.

Figure 22:
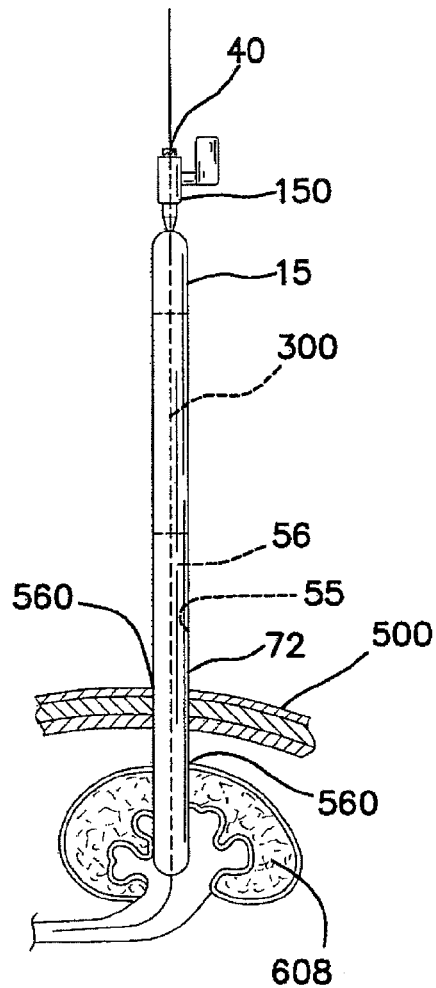
FIG. 22 is a side view depicting the device of FIGS. 16 and 17 with the balloon or sheath expanded and positioned within the body wall and kidney with the distal end of the balloon or sheath positioned in the renal pelvis, the cannula positioned proximal the body wall, and the guide wire in place.
Figure 23:
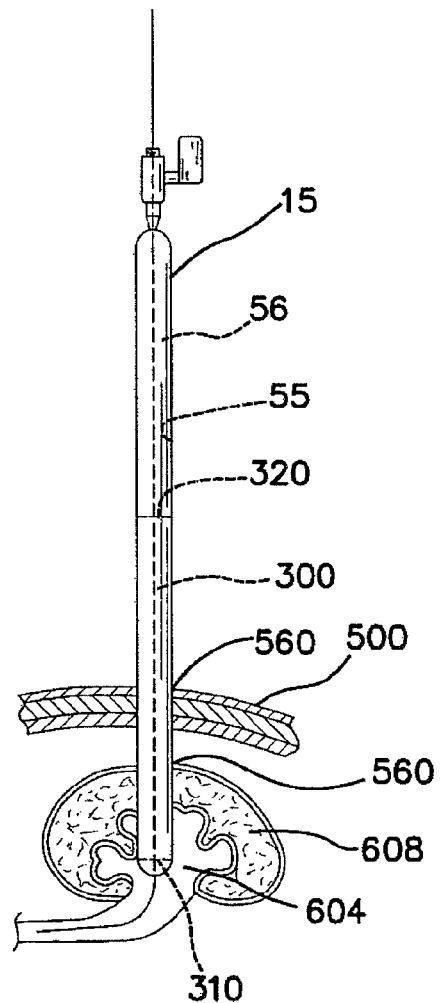
FIG. 23 is a side view depicting the device of FIGS. 16 and 17 with the cannula advanced through the expanded balloon or sheath to a second, distal portion of the balloon or sheath and across the body wall with the distal end of the cannula positioned within the renal pelvis, the proximal end of the cannula positioned proximal the body wall, and the guide wire in place.
Figure 24:
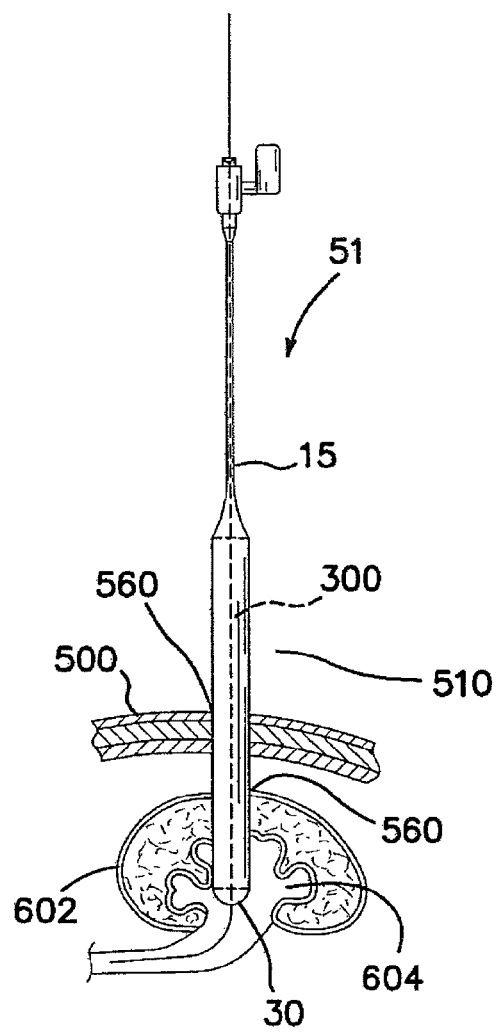
FIG. 24 is a side view depicting the balloon or sheath unexpanded with the balloon or sheath and the cannula positioned across the body wall, the distal ends of the balloon or sheath and the cannula positioned within the renal pelvis, and the guide wire in place.
Figure 25:
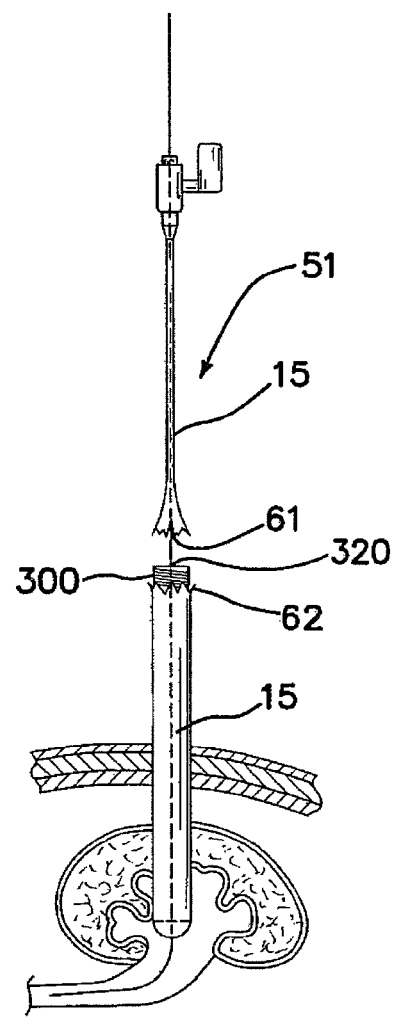
FIG. 25 is a side view depicting a proximal portion of the balloon or sheath separated and removed from the cannula.

When the tamponade trocar device 10 is sufficiently advanced, the stylet 200 may be removed proximally from the proximal end 40 of the balloon 15 or the valve 150 (FIG. 21). A pressurizing or filling source (not shown) is coupled to the proximal end 40 of the balloon 15 or to the valve 150 and the balloon is pressurized to the second, substantially fixed, large diameter condition 72 (FIG. 22). At this stage, the perforation 560 in the body wall 500 and kidney wall 608 is fully dilated and in compressive tamponade. The inside diameter 55 of the balloon 15 allows for the free movement of the cannula 300 that has been provided in the lumen 56 of the balloon. With the balloon 15 expanded and the stylet 200 removed, the cannula 300 may be advanced distally within the lumen 56 of the balloon so that the cannula is positioned across the body wall 500 and kidney wall 608 with the proximal end 320 of the cannula positioned proximal the body wall and the distal end 310 of the cannula positioned within the renal pelvis 604 (FIG. 23).

With the distal end 30 of the balloon 15 intact, there is no communication between the exterior 510 of the biological body 500 and the renal pelvis 604 of the kidney 602 through the perforation 560 via the cannula 300. The balloon 15 is deflated (FIG. 24) or, as is the case with non-distensible balloons, depressurized to ambient pressure. The deflated, unexpanded, balloon 15 is severed (FIG. 25) at a position 61 proximate the proximal end 320 of the cannula 300 and the portion of the balloon proximal the point of severance 62 is removed from the remaining portion of the balloon. The portion 51 of the balloon 15 proximal the point of severance may be discarded.

Figure 26:
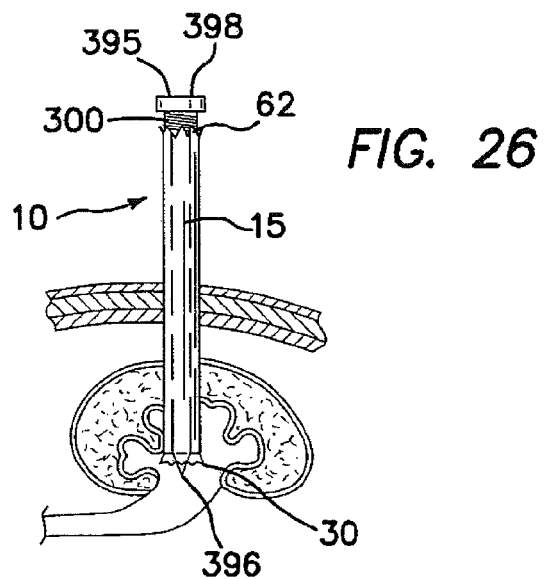
FIG. 26 is a side view depicting the guide wire removed and a piercing device inserted into the lumen of the cannula to pierce the distal end of the balloon or sheath.
Figure 27:
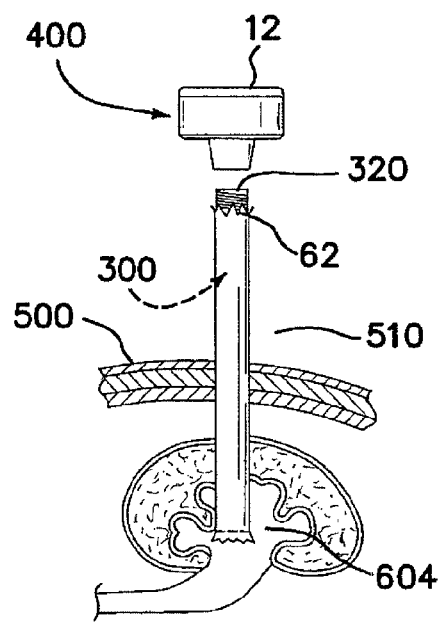
FIG. 27 is a side view depicting the distal end of the balloon after being pierced, the piercing device removed, a seal housing being coupled to the proximal end of the cannula, and the cannula in communication between the renal pelvis and external the body wall.
Figure 28:
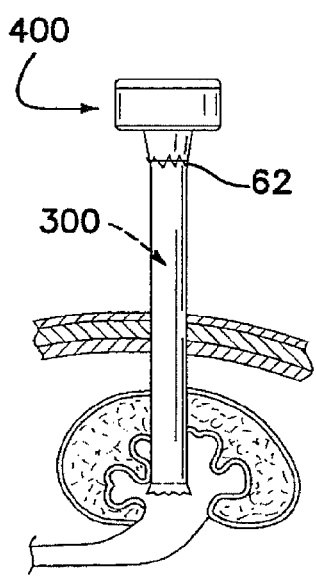
FIG. 28 is a side view depicting the trocar of the present invention placed across the body wall and into the renal pelvis and ready for use as a surgery port.

A piercing member 395 may be provided (FIG. 26). The piercing member 395 includes a proximal end 398 and a distal, puncturing end 396. The piercing member 395 is adapted to fit through the cannula 300 and is of sufficient length to extend the length of the cannula and penetrate the distal end of the balloon 15. The guide wire 600 may be removed proximally from the tamponade trocar device 10 prior to insertion of the piercing member 395 into the cannula 300. The distal end 396 of the piercing member 395 may be inserted into the proximal end 12 of the tamponade trocar device 10 and advanced distally through the tamponade trocar device until the distal, puncturing end of the piercing member punctures and opens the distal end 30 of the balloon 15. The sequence of steps may be adjusted so that the piercing member 395 is placed in the cannula 300 after the final placement of a seal housing 400 in a coupling relationship with the proximal end 320 of the cannula so that there is little or no loss of sealing between outside 510 the biological body 500 and the renal pelvis 604. A trocar seal housing 400 (FIGS. 27 and 28) is coupled to the proximal end 320 of the cannula 300 and the trocar is ready for use as a surgical port.

Many alterations and modifications may be made by those having ordinary skill in the art without departing from the spirit and scope of the invention. For these reasons, the above description should not be construed as limiting the invention, but should be interpreted as merely exemplary of the embodiments. Accordingly, it is not intended that the invention be limited, except as by the appended claims.

We claim:

1. A trocar for insertion through a tissue perforation, comprising:
    an elongate balloon having a proximal end and a distal end; the balloon having a toroid shape that forms a tubular channel throughout the length of the balloon; the tubular channel being connected to an outer body portion of the balloon at the distal end and at the proximal end;
    a cannula positioned inside of the balloon; the cannula having a proximal end, a distal end, and a longitudinal lumen;
    the balloon having a reduced portion located distal to the distal end of the cannula in a first low-profile condition such that the reduced portion has a diameter smaller than the diameter of the distal end of the cannula; the balloon having a second high-profile large diameter condition relative to the first condition; the second high-profile large diameter condition achieved by application of inflation pressure into the balloon; the balloon is adapted to expand from the first low-profile condition to the second high profile condition.

2. The trocar of claim 1 wherein the balloon surrounds the tubular channel.

3. The trocar of claim 1 wherein the tubular channel is located inside the lumen of the cannula.

4. The trocar of claim 1 wherein the reduced portion of the balloon is adapted for insertion into a tissue perforation before insertion of the cannula into the tissue perforation.

5. The trocar of claim 1 wherein when in the second high-profile condition, the reduced portion is expanded to facilitate movement of the cannula relative to the balloon into a position in the tissue perforation while inside the balloon lumen.

6. The trocar of claim 1 wherein the distal reduced portion substantially prevents distal translation of the cannula within the balloon in the first low profile condition.

7. The trocar of claim 1 wherein the distal reduced portion has an increased diameter in the second high profile condition such that the cannula is substantially free to translate within the balloon.

8. The trocar of claim 1 wherein the proximal end of the cannula is distal to the proximal end of the balloon to define a proximal reduced portion of the balloon in the first low profile condition; the proximal reduced portion of the balloon being proximal to the proximal end of the cannula and having a diameter smaller than the diameter of the cannula substantially preventing the proximal translation of the cannula within the balloon in the first low-profile condition.

9. The trocar of claim 1 further including a seal housing attachable to the proximal end of the cannula.

10. The trocar of claim 1 wherein the balloon is inflatable from the first low profile condition to the second high profile condition by application of inflation pressure at the proximal end of the balloon.

11. The trocar of claim 1 further including a stylet configured to provide columnar strength to the balloon for insertion of the distal end of the balloon into the tissue perforation.

12. A method comprising:
providing a system comprising:
a balloon having a proximal end and a distal end; the balloon having a toroid shape that forms a tubular channel extending between an opening at the proximal end and an opening at the distal end;
a cannula having a lumen extending between an open proximal end and an open distal end; the cannula being contained with in the balloon such that the tubular channel extends through the lumen of the cannula;
the balloon having a first low-profile condition and a second high-profile condition; the balloon having a reduced distal portion that is located distal to the distal end of the cannula in the first low-profile condition;
placing the reduced distal portion of the balloon that does not contain the cannula within a tissue perforation in a biological body wall;
inflating the balloon from the first low-profile condition to the second high-profile while the distal portion of the balloon that does not contain the cannula is located in the tissue perforation to increase the size of the balloon and dilate the tissue perforation; and
moving the cannula inside the balloon when in the second high-profile condition.

13. The method of claim 12 wherein the step of moving the cannula includes moving the cannula from a position wherein the distal end of the cannula is proximal to the tissue perforation to a position in which the cannula is within the tissue perforation while in the second high-profile condition.

14. The method of claim 12 wherein the step of moving the cannula includes advancing the cannula distally within the lumen of the balloon so that the cannula is positioned across the body wall with the proximal end of the cannula positioned proximal the body wall and the distal end of the cannula positioned distal the body wall.

15. The method of claim 12 further including a step of deflating the balloon from the second high-profile condition to the first low-profile condition.

16. The method of claim 12 further including a step of severing the balloon at a position proximate the proximal end of the cannula, and a step of removing a portion of the balloon that is proximal to the point of severance.

17. The method of claim 12 further including a step of coupling a seal housing having a seal to the proximal end of the cannula.

18. The method of claim 12 further including a step of penetrating the distal end of the balloon at a location distal to the cannula to create an opening for accessing the cannula lumen from the cannula distal end.

19. The method of claim 12 further including a step of inserting a needle into the body wall to form a tissue perforation.

20. The method of claim 12 further including a step of providing a stylet and inserting the stylet into the tubular channel.

* * * * *